United States Patent [19]

Buschmann et al.

[11] Patent Number: 4,705,553
[45] Date of Patent: Nov. 10, 1987

[54] METHOD OF REDUCING PLANT GROWTH HEIGHT USING PHENYLALKYLMORPHOLINES

[75] Inventors: Ernst Buschmann, Ludwigshafen; Walter Himmele, Walldorf; Heinz Eckhardt; Hansgeorg Ernst, both of Ludwigshafen; Wilhelm Rademacher; Johann Jung, both of Limburgerhof, all of Fed. Rep. of Germany

[73] Assignee: BASF Aktiengesellschaft, Fed. Rep. of Germany

[21] Appl. No.: 15,542

[22] Filed: Feb. 13, 1987

Related U.S. Application Data

[62] Division of Ser. No. 743,683, Jun. 11, 1985, abandoned.

[30] Foreign Application Priority Data

Jun. 12, 1984 [DE] Fed. Rep. of Germany ....... 3421810

[51] Int. Cl.$^4$ ............................................. A01N 43/84
[52] U.S. Cl. ........................................ 71/76; 544/178; 544/59; 546/192
[58] Field of Search ............................ 544/178; 71/76

[56] References Cited

U.S. PATENT DOCUMENTS

| 2,636,036 | 4/1953 | Du Bois et al. ...................... 544/178 |
| 3,649,627 | 3/1972 | Fuerst et al. ......................... 544/178 |
| 4,068,077 | 1/1978 | Goetz et al. ......................... 544/178 |
| 4,202,894 | 3/1980 | Pfiffner .............................. 544/178 |
| 4,241,058 | 12/1980 | Pfiffner .............................. 544/178 |
| 4,277,501 | 7/1981 | Molloy et al. ....................... 424/330 |
| 4,283,534 | 8/1981 | Goetz et al. ......................... 544/178 |
| 4,301,284 | 11/1981 | Buschmann et al. ................ 544/178 |
| 4,602,930 | 7/1986 | Buschmann et al. ................... 71/76 |

FOREIGN PATENT DOCUMENTS

| 7093 | 1/1980 | European Pat. Off. . |
| 51-15627 | 2/1976 | Japan . |
| 807836 | 1/1959 | United Kingdom . |
| 2056454 | 3/1981 | United Kingdom . |

OTHER PUBLICATIONS

Bacchetti et al, Chemical Abstracts, vol. 63, (1965), col. 8346h–8347b.
Chem. Abstracts, vol. 94, No. 21, 1981, p. 735, No. 17 51 36s.

Primary Examiner—Robert W. Ramsuer
Attorney, Agent, or Firm—Keil & Weinkauf

[57] ABSTRACT

Novel phenylalkylcycloamines, their preparation, agents containing these compounds, and methods for regulating plant growth.

1 Claim, No Drawings

METHOD OF REDUCING PLANT GROWTH HEIGHT USING PHENYLALKYLMORPHOLINES

This application is a division of application Ser. No. 743,683, filed on June 11, 1985, now abandoned.

German Laid-Open Application Nos. DOS 2,752,096, DOS 2,656,747, DOS 2,720,612, DOS 2,753,278 and DOS 2,830,127 and European Patent No. 5,541 disclose that phenylpropylamines possess fungicidal activity. These compounds have only an insignificant effect on plant growth.

We have found that extending the propylene radical connecting the two ring structures, which therefore leads to substances of the formula I

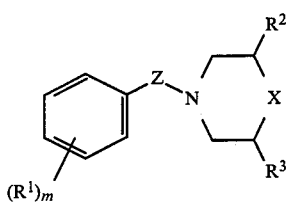

where the radicals $R^1$ are identical or different substituents and are each selected from the group consisting of lower alkyl, cycloalkyl, alkoxy, lower acyl and halogen, $R^2$ and $R^3$ are each hydrogen or $C_1$-$C_3$-alkyl, z is straight-chain $C_4$-$C_{10}$-alkylene which is unsubstituted or substituted by not more than three $C_1$-$C_4$-alkyl radicals, X is oxygen, sulfur or $(CH_2)_p$, m is 0 to 3 and p is 0 to 2, gives compounds which have little or no fungicidal activity but instead surprisingly exhibit interesting growth-regulating actions.

$R^1$ is, for example, $CH_3$, $C_2H_5$, n-propyl, isopropyl, n-butyl, isobutyl, tert.-butyl, tert.-amyl, 1,1-dimethylbutyl, 1,1-dimethylpentyl, cyclopentyl, cyclohexyl, cycloheptyl, norbornyl, methoxy, ethoxy, propoxy, tert.-butoxy, acetyl, propionyl, benzoyl, pivaloyl, F, Cl, Br or I.

$R^2$ and $R^3$ independently of one another are each hydrogen, methyl, ethyl, propyl or isopropyl.

z is, for example, $(CH_2)_4$, $CH_2CHCH_3CH_2CH_2$, $(CH_2)_5$, $CH_2CH_2CHCH_3CH_2CH_2$, $(CH_2)_3CHCH_3CH_2$, $CH_2CHCH_3CH_2CHCH_3CH_2$, $(CH_2)_6$, $(CH_2)_4CHCH_3CH_2$, $(CH_2)_7$, $(CH_2)_5CHCH_3CH_2$, $(CH_2)_8$, $(CH_2)_9$ or $(CH_2)_{10}$.

Examples of amino radicals of the formula I are those derived from pyrrolidine, piperidine, 3-methylpiperidine, 3,5-dimethylpiperidine, morpholine, 2,6-cis-dimethylmorpholine, 2,6-transdimethylmorpholine, 2,6-dimethylthiamorpholine and hexamethyleneimine.

The novel compounds can be used as active ingredients in growth regulators.

For the purposes of the present invention, important intermediate compounds for the preparation of phenylalkylamines are phenylalkyl halides of the formula II

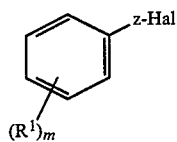

which in turn can be prepared by, for example, condensation reactions or other reactions to form C-C bonds, as shown in equation 1.

EQUATION 1

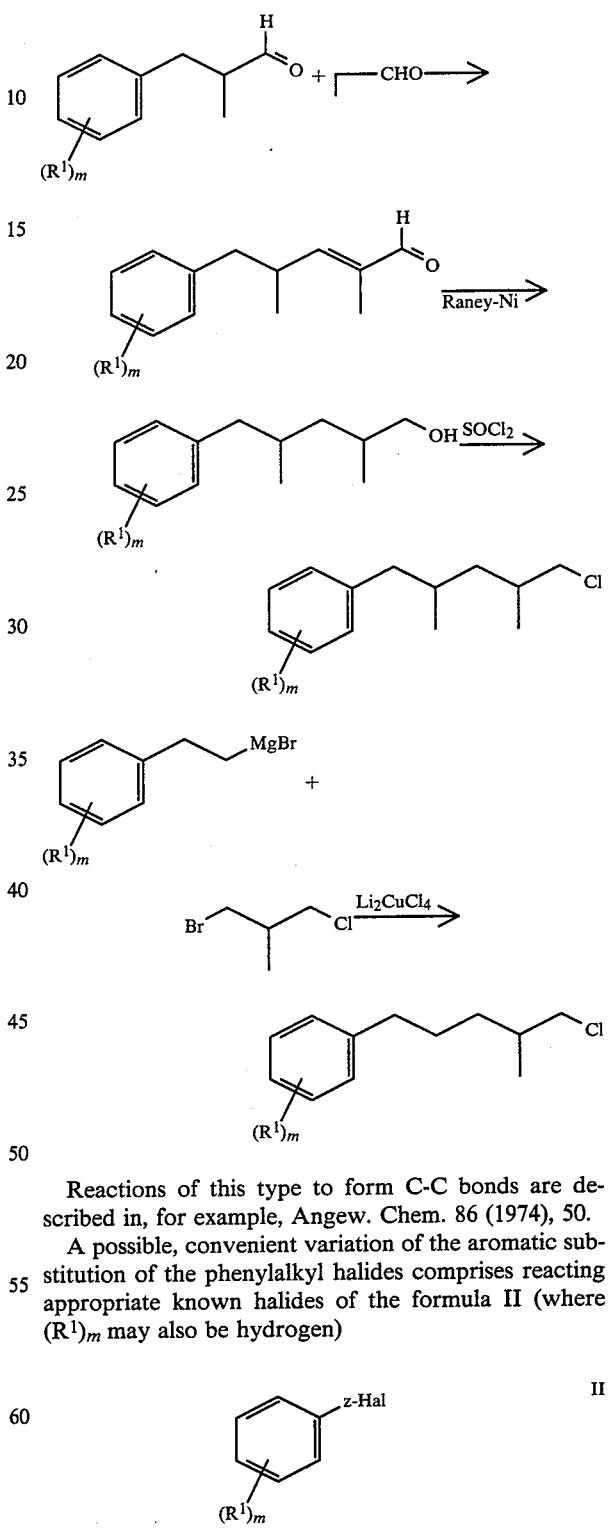

Reactions of this type to form C-C bonds are described in, for example, Angew. Chem. 86 (1974), 50.

A possible, convenient variation of the aromatic substitution of the phenylalkyl halides comprises reacting appropriate known halides of the formula II (where $(R^1)_m$ may also be hydrogen)

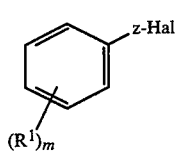

in which halogen is preferably chlorine but may furthermore be bromine or iodine, some of these halides being available commercially.

The preparation process described below can be carried out using these halides.

EQUATION 2

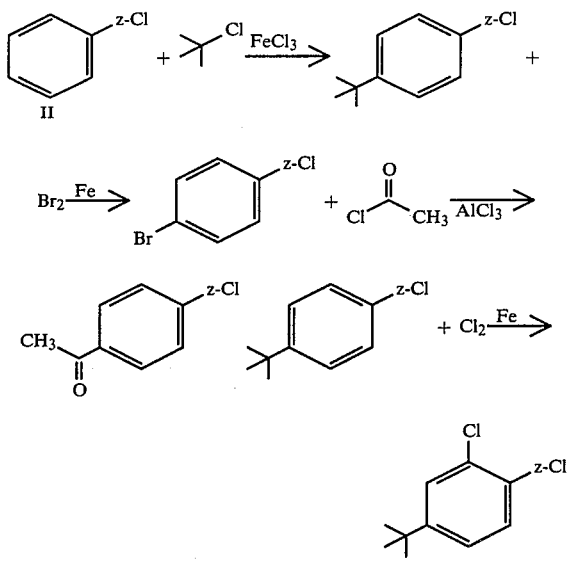

The synthesis of appropriate phenylpropyl halides, which are described in European Patent No. 9,077, can also be extrapolated without difficulty to phenylalkyl chlorides possessing a longer chain.

Reaction of the corresponding phenylalkyl halides (II)

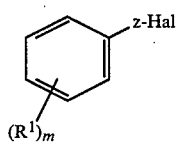

with the secondary cyclic amines (IV)

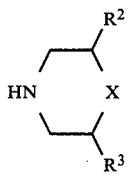

gives the phenylalkylamines according to the invention.

The reaction of (II) with (IV) takes place spontaneously in the presence or absence of a solvent, at in general from 50° to 200° C., preferably from 130° to 170° C. Suitable solvents are tetrahydrofuran, toluene, xylene, dimethylformamide and dimethylacetamide. It is sometimes advantageous to add a neutralizing agent, such as $Na_2CO_3$, $K_2CO_3$ or $NaHCO_3$, to the reaction mixture.

PREPARATION EXAMPLES FOR INTERMEDIATES

A. 2,4-Dimethyl-4-phenylbutyl chloride (a) 192 g of propionaldehyde are added dropwise to a solution of 402 g of 2-phenylpropan-1-al and 12 g of sodium hydroxide in 1 l of methanol in the course of 6 hours. Stirring is continued for one hour, after which the mixture is neutralized with glacial acetic acid (pH=6), stirred overnight and evaporated down, the residue is taken up with $CH_2Cl_2/H_2O$, and the solution is extracted with $CH_2Cl_2$. The organic phase is washed with water, dried over $Na_2SO_4$, evaporated down again and distilled to give 178 g of 2,4-dimethyl-4-phenylbut-2-en-1-al of boiling point 108°–120° C./0.5 mbar.

(b) The aldehyde obtained (178 g of 2,4-dimethyl-4-phenylbut-2-en-1-al) is hydrogenated in 600 ml of methanol with 40 g of Raney nickel at from 60° to 70° C. and under a hydrogen pressure of 100 bar. The catalyst is filtered off, the filtrate is evaporated down and the residue is distilled to give 137 g of 2,4-dimethyl-4-phenylbutan-1-ol. The reactions are repeated in order to produce a larger stock.

(c) 219 g of 2,4-dimethyl-4-phenyl-butan-1-ol are added dropwise to 161 g of thionyl chloride, the mixture is stirred overnight at room temperature and then for 2 hours at 140° C., and the crude product is distilled to give 150 g of 2,4-dimethyl-4-phenylbutyl chloride of boiling point 84°–86° C./0.1 mm.

B. 2-Methyl-5-phenylpentyl chloride 0.26 mole of 3-bromo-2-methylpropyl chloride in 50 ml of tetrahydrofuran is added dropwise to a suspension of 0.45 mole of phenylethylmagnesium chloride in 500 ml of tetrahydrofuran at −15° C. 13 ml of a 0.5 molar solution of $Li_2CuCl_4$ in tetrahydrofuran are then added dropwise at −15° C.

The mixture is heated to room temperature and 360 ml of saturated $NH_4Cl$ solution are added, after which the mixture is extracted with ether, the solution is dried over $Na_2SO_4$ and evaporated down, and the residue is distilled to give 30 g of 2-methyl-5-phenylpentyl chloride of boiling point 83°–87° C./0.1 mbar (the procedure is repeated).

C. 5-p-tert.-Butylphenyl-2-methylpentyl chloride 27 g of tert.-butyl chloride are added dropwise to an ice-cooled mixture of 52 g of 2-methyl-5-phenylpentyl chloride and 4.9 g of $FeCl_3$. The mixture is stirred for 7 hours at 50° C. and for 12 hours at room temperature, and taken up in methylene chloride, the solution is washed with water, dried over $Na_2SO_4$ and evaporated down, and the residue is distilled to give 40 g of 5-p-tert.-butylphenyl-2-methylphenyl chloride of boiling point 114°–118° C./0.2 mbar.

The phenylalkyl chlorides of the formula (II) which are summarized in the Table below can be prepared from known intermediates in accordance with the Examples above.

TABLE 1

Phenylalkyl halides

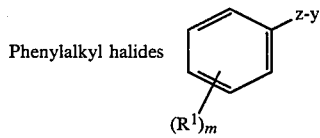

| Compound No. | $(R^1)_m$ | -z- | y | bp. °C./mbar |
|---|---|---|---|---|
| 1 | H | $(CH_2)_4$ | Br | 76° 0,4 |
| 2 | 4-tBu | $(CH_2)_4$ | Cl | |
| 3 | 4-Br | $(CH_2)_4$ | Cl | |
| 4 | H | $CHCH_3CH_2CHCH_3CH_2$ | Cl | 84–6° 0.1 |
| 5 | 4-acetyl | $(CH_2)_4$ | Br | |
| 6 | 4-$OCH_3$ | $(CH_2)_5$ | Cl | |
| 7 | H | $(CH_2)_5$ | Br | 78–80° 0.2 |
| 8 | 4-t-Bu | $(CH_2)_5$ | Cl | 112–115° 0.4 |
| 9 | 4-Cl | $(CH_2)_5$ | Cl | 106–112° 0.2 |
| 10 | 4-$CH_3$ | $(CH_2)_5$ | Cl | 116–122° 0.8 |

TABLE 1-continued

Phenylalkyl halides (structure with Z-Y substituent and $(R^1)_m$)

| Compound No. | $(R^1)_m$ | -z- | y | bp. °C./mbar |
|---|---|---|---|---|
| 11 | H | $(CH_2)_2CHCH_3(CH_2)_2$ | Cl | 80–82° 0.2 |
| 12 | H | $(CH_2)_3CHCH_3CH_2$ | Cl | 83–87° 0.2 |
| 13 | 4-t-Bu | $(CH_2)_3CHCH_3CH_2$ | Cl | 120–2° 0.2 |
| 14 | 2-$CH_3$ | $(CH_2)_5$ | Cl | 90–91° 0.2 |
| 15 | 4-cyclohexyl | $(CH_2)_5$ | Br | |
| 16 | 4-propionyl | $(CH_2)_5$ | Cl | |
| 17 | H | $(CH_2)_6$ | Cl | 86–90° 0.3 |
| 18 | H | $(CH_2)_4CHCH_3CH_2$ | Cl | 116–120° 0.2 |
| 19 | 4-Br | $(CH_2)_6$ | Cl | |
| 20 | 4-$OCH_3$ | $(CH_2)_6$ | Cl | |
| 21 | 4-OtBu | $(CH_2)_6$ | Cl | |
| 22 | 4-cyclohexyl | $(CH_2)_6$ | Cl | |
| 23 | 4-tBu | $(CH_2)_4CHCH_3CH_2$ | Cl | 130° 0.1 mm |
| 24 | 4-tBu | $(CH_2)_6$ | Cl | 120–2° 0.2 mm |
| 25 | 4-tBu | $CH_2CHCH_3(CH_2)_4$ | Cl | |
| 26 | 4-$CH_3$ | $CH_2CHCH_3(CH_2)_4$ | Cl | |
| 27 | 4-t-amyl | $CH_2CHCH_3(CH_2)_4$ | Cl | |
| 28 | 2,4-$Cl_2$ | $CH_2CHCH_3(CH_2)_4$ | Cl | |
| 29 | 2,3,4-$Cl_3$ | $CH_2CHCH_3(CH_2)_4$ | Cl | |
| 30 | H | $(CH_2)_7$ | Cl | 116–122° 0.1 |
| 31 | 4-tBu | $(CH_2)_7$ | Cl | |
| 32 | H | $(CH_2)_{10}$ | Cl | |

If the method below is appropriately modified, the phenylalkyl halides of the formula (II) can be converted to the phenylalkylamines of the formula (I).

PREPARATION EXAMPLE FOR A COMPOUND ACCORDING TO THE INVENTION

N-(2-Methyl-5-phenylpentyl)-2,6-cis-dimethylmorpholine 20 g of 2-methyl-5-phenylpentyl chloride and 35 g of 2,6-cis-dimethylmorpholine are heated at 150° C. for 10 hours, after which the mixture is left to cool, taken up with $CH_2Cl_2$, washed with water, dilute NaOH and once again with water, dried over $Na_2SO_4$ and evaporated down, and the residue is distilled to give 18 g of a product of boiling point 130°–132° C./0.4 mbar.

The phenylalkyl halides, for example those shown in Table 1, can be converted to novel phenylalkylamine of the formula I (Table 2) by a similar method; those compounds which are characterized by physical data have been prepared, and their biological action investigated. The compounds which are not characterized are expected, on the basis of structural similarity, to have a similar action.

TABLE 2

Phenylalkylamines (structure with Z-N, X, $R^2$, $R^3$ and $(R^1)_m$)

| Compound No. | $(R^1)_m$ | -z- | X | $R^2$ | $R^3$ | bp. °C./mbar |
|---|---|---|---|---|---|---|
| 101 | H | $(CH_2)_4$ | $CH_2$ | H | H | 116–120°/0.3 |
| 102 | 4-tBu | $(CH_2)_4$ | O | $CH_3$ | $CH_3$ | |
| 103 | 4-Br | $(CH_2)_4$ | O | $CH_3$ | $CH_3$ | |
| 104 | H | $(CH_2)_5$ | O | $CH_3$ | $CH_3$ | 134–6°/0.1 m |
| 105 | H | $(CH_2)_5$ | $CH_2$ | H | $CH_3$ | |
| 106 | 4-$OCH_3$ | $(CH_2)_5$ | $CH_2$ | H | H | |
| 107 | H | $(CH_2)_5$ | O | $C_2H_5$ | $C_2H_5$ | |
| 108 | H | $(CH_2)_3CHCH_3CH_2$ | O | $CH_3$ | $CH_3$ | 130–2°/0.4 |
| 109 | 4-Cl | $(CH_2)_5$ | — | H | H | |
| 110 | 4-tBu | $(CH_2)_5$ | O | $CH_3$ | $CH_3$ | 165–8°/0.3 |
| 111 | 4-tBu | $(CH_2)_3CHCH_3CH_2$ | O | $CH_3$ | $CH_3$ | 149–153/0.2 |
| 112 | 4-tBu | $(CH_2)_3CHCH_3CH_2$ | S | $CH_3$ | $CH_3$ | |
| 113 | 4-tBu | $(CH_2)_3CHCH_3CH_2$ | $CH_2$ | $CH_3$ | $CH_3$ | |
| 114 | 4-tBu | $CH_2CHCH_2CH-CH_2$ with $CH_3$, $CH_3$ branches | O | $CH_3$ | $CH_3$ | |
| 115 | 4-tBu | $CH_2CHCH_2CH-CH_2$ with $CH_3$, $CH_3$ branches | $CH_2$ | $CH_3$ | $CH_3$ | 166–172°/0.1 |
| 116 | 4-$CH_3$ | $(CH_2)_5$ | O | $CH_3$ | $CH_3$ | 140–2°/0.3 |
| 117 | 4-cyclohexyl | $(CH_2)_5$ | O | $CH_3$ | $CH_3$ | |
| 118 | 4-acetyl | $(CH_2)_4$ | O | $CH_3$ | $CH_3$ | |
| 119 | H | $(CH_2)_6$ | O | $CH_3$ | $CH_3$ | 128–130°/0.1 |
| 120 | H | $(CH_2)_6$ | $CH_2$ | H | $CH_3$ | |
| 121 | H | $(CH_2)_4CHCH_3CH_2$ | O | $CH_3$ | $CH_3$ | 135–8°/0.2 |
| 122 | 4-OtBu | $(CH_2)_6$ | O | $CH_3$ | $CH_3$ | |

TABLE 2-continued

Phenylalkylamines

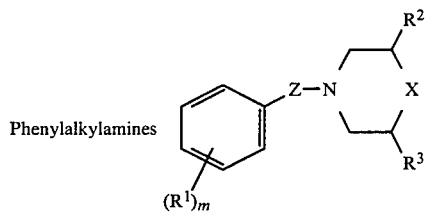

| Compound No. | $(R^1)_m$ | -Z- | X | $R^2$ | $R^3$ | bp. °C./mbar |
|---|---|---|---|---|---|---|
| 123 | 4-cyclohexyl | $(CH_2)_6$ | O | $CH_3$ | $CH_3$ | |
| 124 | 4-tBu | $(CH_2)_6$ | O | $CH_3$ | $CH_3$ | 162–5°/0.2 |
| 125 | 4-tBu | $(CH_2)_6$ | O | H | H | |
| 126 | 4-tBu | $(CH_2)_6$ | $CH_2$ | H | H | |
| 127 | 4-tBu | $(CH_2)_4CHCH_3CH_2$ | O | $CH_3$ | $CH_3$ | 159–160°/0.2 |
| 128 | 4-tBu | $(CH_2)_4CHCH_3CH_2$ | $CH_2$ | H | H | |
| 129 | 4-tBu | $CH_2CHCH_3(CH_2)_4$ | O | $CH_3$ | $CH_3$ | |
| 130 | 4-t-amyl | $CH_2CHCH_3(CH_2)_4$ | O | $CH_3$ | $CH_3$ | |
| 131 | 2,4-$Cl_2$ | $CH_2CHCH_3(CH_2)_4$ | O | $CH_3$ | $CH_3$ | |
| 132 | 2,3,4-$Cl_3$ | $CH_2CHCH_3(CH_2)_4$ | O | $CH_3$ | $CH_3$ | |
| 133 | H | $(CH_2)_7$ | O | $CH_3$ | $CH_3$ | 148–152°/0.2 |
| 134 | 4-tBu | $(CH_2)_7$ | $CH_2$ | H | H | |
| 135 | 4-tBu | $(CH_2)_7$ | O | $CH_3$ | $CH_3$ | |
| 136 | H | $(CH_2)_{10}$ | O | $CH_3$ | $CH_3$ | |
| 137 | 4-tBu | $(CH_2)_2CHCH_3(CH_2)_2$ | O | $CH_3$ | $CH_3$ | 145–150/0.1 |
| 138 | H | $(CH_2)_3CHC_2H_5CH_2$ | O | $CH_3$ | $CH_3$ | 160–162/0.7 |
| 139 | H | $CHCH_3CH_2CHC_2H_5CH_2$ | O | $CH_3$ | $CH_3$ | 128–133/0.5 |
| 140 | H | $CHCH_3CH_2CHCH_3CH_2$ | O | $CH_3$ | $CH_3$ | 134–138/0.7 |
| 141 | H | $(CH_2)_2(CHCH_3)_2CH_2$ | O | $CH_3$ | $CH_3$ | 140–142/0.7 |

For example, the growth-regulating action of the novel phenylalkylamines can be determined in the manner described below.

1. Rice seedling test

The test procedure is described by W. Rademacher and J. Jung in Z. Acker- und Pflanzenbau 150 (1981), 363–371. This test is used to characterize growth-regulating activity. The compounds 110, 111 and 124 showed a substantially superior shortening action compared with the standard compounds chlormequat chloride and fenpropimorph.

Concentrations of active ingredient (mole/l) which result in 50% shortening of the second leaf sheath in rice seedlings (Girona variety)

| Active ingredient | Concentration |
|---|---|
| chlormequat chloride | $1.5 \times 10^{-2}$ |
| fenpropimorph | $1.0 \times 10^{-4}$ |
| compound 110 | $1.4 \times 10^{-5}$ |
| compound 111 | $3.5 \times 10^{-5}$ |
| compound 116 | $1.9 \times 10^{-5}$ |
| compound 124 | $2.7 \times 10^{-5}$ |

2. Sunflowers—postemergence method

Sunflowers of the Spanners Allzweck variety were grown on culture substrates provided with sufficient nutrients, in plastic vessels having a diameter of about 12.5 cm. The novel compounds to be tested, in the form of an aqueous formulation, were sprayed onto the plants after emergence. The growth-regulating action observed was confirmed at the end of the experiment by measuring the height of growth. The measured values thus obtained were expressed as a ratio of the height of growth of the untreated plants.

For treatment with, for example, 6 mg of active ingredient per vessel, the amines 110, 111, 121, 127 and 137 showed a superior shortening action compared with the standard compounds cycocel and fenpropimorph.

| Active ingredient | Height of shoot (% of control) |
|---|---|
| chlormequat chloride | 87.5 |
| fenpropimorph | 81.0 |
| compound 110 | 74.5 |
| compound 111 | 71.3 |
| compound 121 | 71.3 |
| compound 127 | 76.1 |
| compound 137 | 70.7 |
| control | 100 |

3. Seed treatment in the case of wheat, barley and corn

Treatment of the seed of wheat (Kolibri variety), barley (Aramir variety) and corn (Inrakorn variety) with 1 g of active ingredient per kg of seed resulted in a pronounced reduction in the height of growth. In this respect, compound No. 111, in particular, proved superior to the standard compounds chlormequat chloride and fenpropimorph.

| (Data as a percentage of the particular control) | | | |
|---|---|---|---|
| Active ingredient | Wheat | Barley | Corn |
| chlormequat chloride | 87 | 96 | 100 |
| fenpropimorph | 92 | 91 | 101 |
| compound 111 | 24 | 57 | 63 |

We claim:

1. A method of reducing the growth height in plants, which comprises allowing an effective amount of phenylalkylamine of the formula

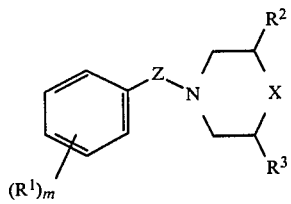

where the radical $R^1$ is selected from the group consisting of lower alkyl, $R^2$ and $R^3$ are $C_1$–$C_3$-alkyl, z is a straight-chain $C_4$–$C_{10}$-alkylene which is unsubstituted or substituted by not more than three $C_1$–$C_4$-alkyl radicals, X is oxygen, and m is 1, to act on plants or on their propagation stock.

* * * * * where the radical $R^1$ is selected from the group consisting of lower alkyl, $R^2$ and $R^3$ are $C_1$–$C_3$-alkyl, z is a straight-chain $C_4$–$C_{10}$-alkylene which is unsubstituted or substituted by not more than three $C_1$–$C_4$-alkyl radicals, X is oxygen, and m is 1, to act on plants or on their propagation stock.

* * * * *